United States Patent
Sugahara

[11] Patent Number: 5,997,484
[45] Date of Patent: Dec. 7, 1999

[54] PROBE FOR MEASURING EPIDURAL PRESSURE AND ELASTICITY OF BRAIN PARENCHYMA

[75] Inventor: Tomio Sugahara, Osaka, Japan

[73] Assignee: Sugan Co., Ltd., Osaka, Japan

[21] Appl. No.: 09/006,189

[22] Filed: Jan. 13, 1998

[30] Foreign Application Priority Data

Jan. 13, 1997 [JP] Japan ..................................... 9-003884
May 13, 1997 [JP] Japan ..................................... 9-122170

[51] Int. Cl.$^6$ ....................................................... A61B 5/00
[52] U.S. Cl. ........................... 600/561; 600/587; 73/715; 73/729.1
[58] Field of Search .................................... 600/561, 587; 604/8, 9; 73/708, 714, 715, 729.1

[56] References Cited

U.S. PATENT DOCUMENTS

| | | | |
|---|---|---|---|
| 3,686,958 | 8/1972 | Porter et al. | 600/561 |
| 4,022,190 | 5/1977 | Meyer | 600/561 |
| 4,026,276 | 5/1977 | Chubbuck | 600/561 |
| 4,185,641 | 1/1980 | Minior et al. | 600/561 |
| 4,231,376 | 11/1980 | Lyon et al. | 600/561 |
| 4,312,361 | 1/1982 | Nicholson et al. | 600/561 |
| 4,393,878 | 7/1983 | Kahn | 600/561 |
| 4,471,786 | 9/1984 | Inagaki et al. | 600/561 |
| 4,557,721 | 12/1985 | Hooven | 604/9 |
| 4,593,703 | 6/1986 | Cosman | 600/561 |

FOREIGN PATENT DOCUMENTS 5-115444   5/1993   Japan .

*Primary Examiner*—Max Hindenburg
*Assistant Examiner*—Charles Marmor, II
*Attorney, Agent, or Firm*—McDermott, Will & Emery

[57] ABSTRACT

A probe for measuring epidural pressure and the elasticity of brain parenchyma includes first and second chambers both formed of a thin film with a bag-shape so that they can contract/expand in response to introduction of first and second pressure transmission mediums, respectively, wherein the first and second chambers are independent of each other and provided in a stack. Thus a probe capable of accurately measuring epidural pressure and the elasticity of brain parenchyma can be provided.

5 Claims, 3 Drawing Sheets

PROBE FOR MEASURING EPIDURAL PRESSURE AND ELASTICITY OF BRAIN PARENCHYMA

BACKGROUND OF THE INVENTION

1. Field of the Invention

The present invention relates to probes for measuring epidural pressure and the elasticity of brain parenchyma, and more particularly to a probe for accurately measuring epidural pressure and the elasticity of brain parenchyma for use in the field of diagnosis of the neurosurgery.

2. Description of the Background Art

When a patient is suspected to be suffering from acute cerebral hypertension due to injury in the head, infarct edema, intracerebral hemorrhage or the like, or a patient has chronic cerebral hypertension such as hydrocephalus, measuring intracranial pressure, that is, cerebral pressure is particularly important to know the patient's condition and to carry out surgical treatment.

As a method of measuring a cerebral pressure, measuring the epidural pressure of the patient using a cerebral pressure measuring apparatus has been proposed. This epidural pressure closely relates to increase/decrease in intradural pressure, wherein the epidural pressure increases with increase in intradural pressure due to tumefaction of brain parenchyma and decreases with decrease therein, for example.

Accordingly, in order to observe the brain condition of the patient which is changing every moment, it is extremely useful to measure not only the epidural pressure but also the elasticity of brain parenchyma itself. Then, as apparatus for measuring the elasticity of brain parenchyma, Japanese Patent Laying-Open No. 5-115444 discloses an apparatus for measuring both epidural pressure and the elasticity of brain parenchyma.

This apparatus for measuring the elasticity of brain parenchyma disclosed in Japanese Patent Laying-Open No. 5-115444, however, has the following problems.

According to this measuring apparatus, a chamber formed of a thin film with a bag-shape is provided at one end of a flexible hollow tube, which chamber is inserted outside a dura through an opening formed in the patient's cranium. Then, the chamber is filled with air by means of a plunger pump or the like, whereby epidural pressure is measured from the pressure applied to the chamber, using a measuring apparatus provided at the other end of the tube. A small amount of air is further introduced into the chamber and thereafter change in epidural pressure is measured based on the pressure applied to the chamber. Then, the former epidural pressure is compared with the latter, thereby measuring the elasticity of brain parenchyma.

However, epidural pressure is measured by introducing air into a single chamber in stages as described above. Therefore, if the second air introduction is carried out with the epidural pressure in the first cerebral pressure measurement still being applied to the chamber, epidural pressure corresponding to the second air introduction cannot be measured with high precision because of temporary reverse air flow from the chamber, poor response of the chamber to the additional air introduction using a plunger pump or the like.

SUMMARY OF THE INVENTION

It is an object of the present invention to provide a probe for measuring the epidural pressure and the elasticity of brain parenchyma capable of accurately measuring the elasticity of brain parenchyma by measuring with high precision change in the second and the following epidural pressure values based on the first one.

According to the present invention, a probe for measuring epidural pressure and the elasticity of brain parenchyma inserted between cranium and a dura includes a first chamber formed of a thin film with a bag-shape and provided on the side of the cranium so that it can contract/expand in response to introduction of a first pressure transmission medium, a first tube having its one end fixed to the first chamber for introducing the first pressure transmission medium into the first chamber, a second chamber independent of the first chamber, formed of a thin film with a bag-shape and provided on the first chamber on the side of the dura so that it can contract/expand in response to introduction of a second pressure transmission medium, and placed on the first chamber, and a second tube having its one end fixed to the second chamber for introducing the second pressure transmission medium into the second chamber.

Thus, the first chamber and the second chamber are provided in a lamination layer, whereby change in epidural pressure is measured by first introducing the first pressure transmission medium into the first chamber and thereafter the second pressure transmission medium into the second chamber. Thus, change in epidural pressure resulting from pressure of the first chamber changed accurately according to the amount of the second pressure transmission medium introduced into the second chamber can be measured. Accordingly, the accurate elasticity of brain parenchyma can be measured from the resultant change in epidural pressure.

Preferably in the probe for measuring epidural pressure and the elasticity of brain parenchyma, the second chamber has a through hole defining a first auxiliary chamber on the side of the dura, and a second auxiliary chamber on the side of the first chamber and having a through hole at a position approximately opposite to the position to attach the second tube, through the through hole the first and second auxiliary chambers communicate with each other, and the second tube has a first auxiliary tube fixed to the first auxiliary chamber and a second auxiliary tube fixed to the second auxiliary chamber.

Thus, when a liquid is used as the second pressure transmission medium, for example, the liquid may be introduced into the first auxiliary chamber positioned on the side of the dura using the first auxiliary tube while air or the like within the second chamber can be discharged from the side of the second auxiliary chamber using the second auxiliary tube.

As a result, the second chamber can be filled with the liquid, and as with the above invention, change in epidural pressure resulting from pressure of the first chamber which changed accurately according to the amount of the liquid introduced into the second chamber can be measured. Accordingly, the accurate elasticity of brain parenchyma can be measured from the resultant change in epidural pressure.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

A probe for measuring epidural pressure and the elasticity of brain parenchyma according to the present invention will now be described with reference to the drawings.

First Embodiment

Figure 1:
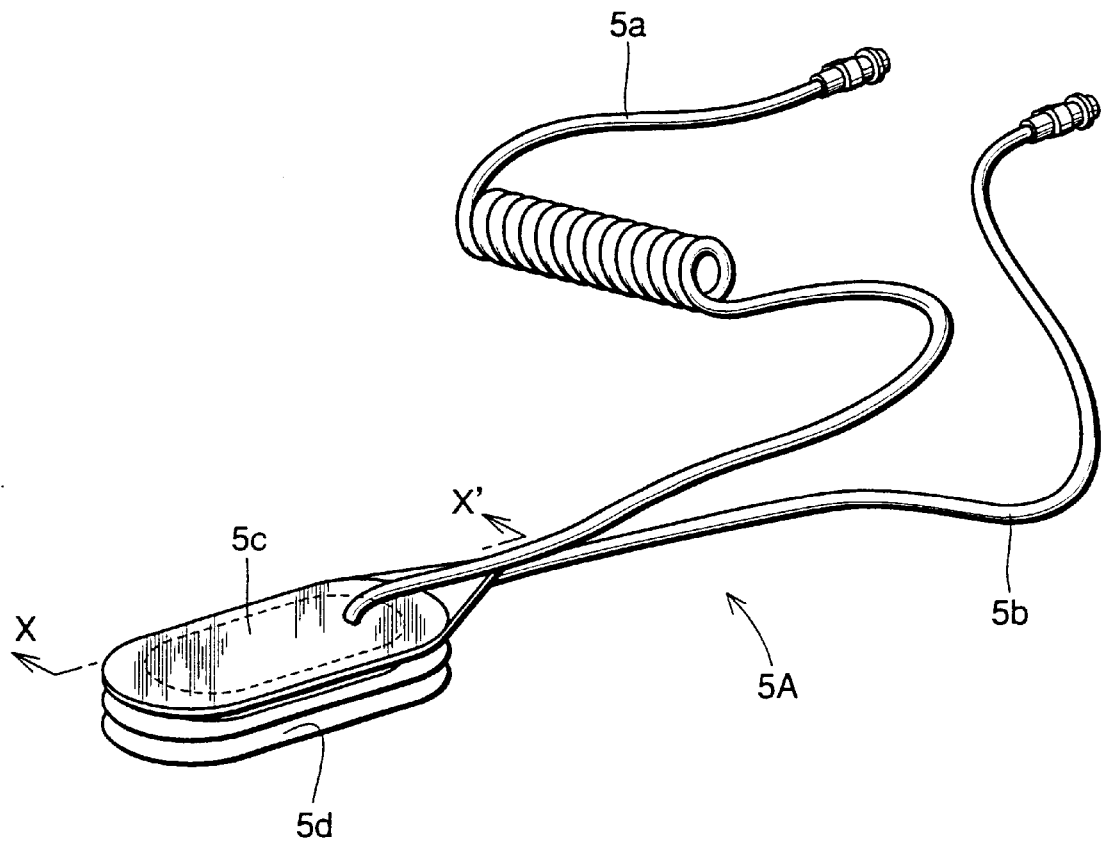
FIG. 1 is a perspective view showing the whole probe for measuring epidural pressure and the elasticity of brain parenchyma according to a first embodiment of the present invention.
Figure 2:
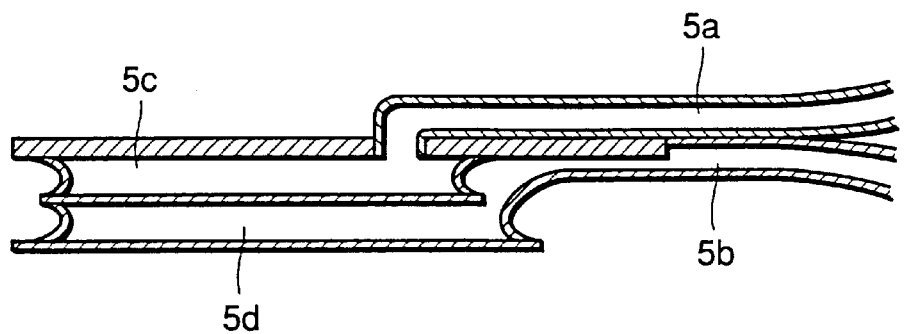
FIG. 2 is a cross sectional view taken along the line X—X' of FIG. 1.

A probe for measuring an epidural pressure and the elasticity of brain parenchyma, according to a first embodiment of the invention will be described with reference to FIGS. 1 and 2.

A measuring probe 5A of the present embodiment includes a first chamber 5c formed of a thin film with a bag-shape so that it can contract/expand in response to introduction/discharge of air, and a second chamber 5d placed on the first chamber 5c also formed of a thin film with a bag-shape so that it can contract/expand in response to introduction/discharge of air as in the case of first chamber 5c. First chamber 5c and second chamber 5d are preferably made of thermoplastic polyurethane, and first chamber 5c has substantial volume of 0.1 ml, while second chamber 5d has variable volume in the range from 0.1 to 2.0 ml.

First and second flexible hollow tubes 5a and 5b are respectively connected to first and second chambers 5c and 5d, whereby air is respectively introduced into first and second chambers 5c and 5d through first and second tubes 5a and 5b. First and second tubes 5a and 5b are also preferably made of thermoplastic polyurethane.

An example of measuring epidural pressure and the elasticity of the brain parenchyma using measuring probe 5A with the above-described structure will now be described with reference to FIG. 3.

First, first chamber 5c and second chamber 5d of measuring probe 5A are inserted between a cranium 7a and a dura 7c through an opening 7b formed in cranium 7a of a patient 7.

First tube 5a with its one end connected to first chamber 5c has the other end connected to an air supply port 4 provided in a measuring apparatus 1 for introducing air into first chamber 5c and measuring epidural pressure applied to first chamber 5c. Measuring apparatus 1 is provided with a power supply switch 2 and a display 3 for displaying an epidural pressure value.

Meanwhile, an air tube injector 6 (1.0 ml) for supplying air into second chamber 5d is connected to the other end of second tube 5b with its one end connected to second chamber 5d.

According to the measuring apparatus with the above-described structure, a prescribed amount of air is first introduced from measuring apparatus 1 into first chamber 5c, whereby epidural pressure applied to first chamber 5c is measured.

Then, a prescribed amount of air is injected into second chamber 5d by air injector 6 with the introduced air within first chamber 5c being maintained, whereby change in epidural pressure displayed on measuring apparatus 1 is measured. The amount of air to be introduced into the second chamber increases corresponding to the elasticity of the patient's brain parenchyma. More specifically, with low elasticity, the measured value of measuring apparatus 1 will rapidly increase, and therefore the elasticity of brain parenchyma can be accurately measured based on the relation between change in a signal of measuring apparatus 1 and increase in the amount of air introduced into second chamber 5d.

More simply, change in epidural pressure is continually displayed on display 3 of measuring apparatus 1, whereby the elasticity of brain parenchyma can be immediately known from both the change rate of the epidural pressure and that of the amount of air within second chamber 5d. More specifically, smaller change in epidural pressure indicates higher elasticity of brain parenchyma in the dura, while larger change in epidural pressure indicates lower elasticity thereof. Note that the amount of air introduced into the second chamber may be increased as appropriate, but it is preferable to measure epidural pressure with the amount of air introduced into the second chamber being increased by about 0.1 to about 1.0 ml.

As has been described above, in the measurement of epidural pressure and the elasticity of brain parenchyma using the measuring probe according to the present embodiment, epidural pressure corresponding to the amount of air introduced into the second chamber can be measured at the first chamber. Accordingly, the elasticity of brain parenchyma can be measured with high precision, whereby doctors can readily and accurately know the condition of brain parenchyma and therefore can provide appropriate treatment and diagnosis according to the patient's condition or the like.

Note that air injector 6 is used to inject air into second chamber 5d in the above-described embodiment, but the present invention is not limited to this and similar effects can be obtained with a mechanical apparatus such as a compressor.

In addition, air is used as the pressure transmission medium introduced into the first and second chambers in the above-described embodiment, the medium is not necessarily limited to air, and use of a gas such as carbonic acid gas may bring about similar effects.

Second Embodiment

Figure 4:
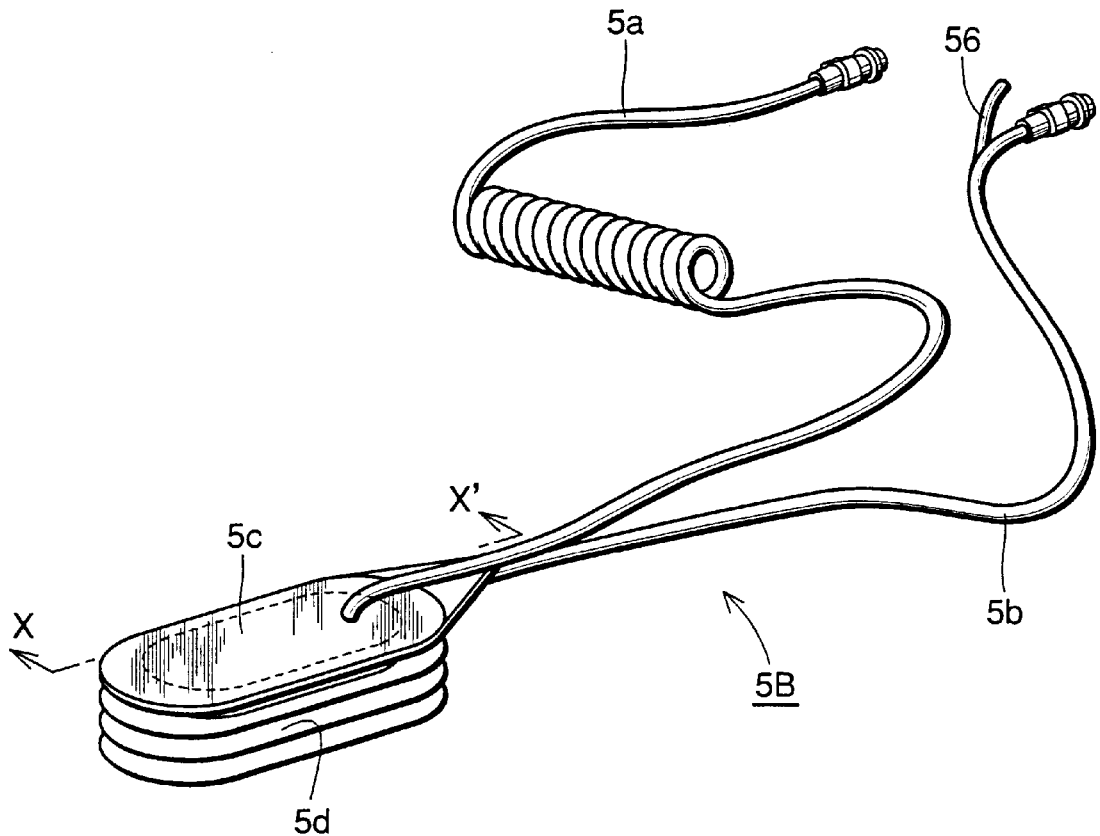
FIG. 4 is a perspective view showing the overall probe for measuring epidural pressure and the elasticity of brain parenchyma, according to a second embodiment of the present invention.

A probe 5B for measuring epidural pressure and the elasticity of brain parenchyma, according to a second embodiment of the invention will be described with reference to FIGS. 4 and 5. FIG. 4 is a perspective view showing probe 5B according to this embodiment, and FIG. 5 is a cross sectional view taken along X—X' in FIG. 4.

Probe 5B for measuring epidural pressure and the elasticity of brain parenchyma, having basically the same structure as probe 5A is particularly suitable for the case in which a liquid is used as a pressure transmission medium to be introduced into its second chamber 5d. Herein, only the structures of second chamber 5d and second tube 5b different from those of probe 5A according to the first embodiment will be described.

Figure 5:
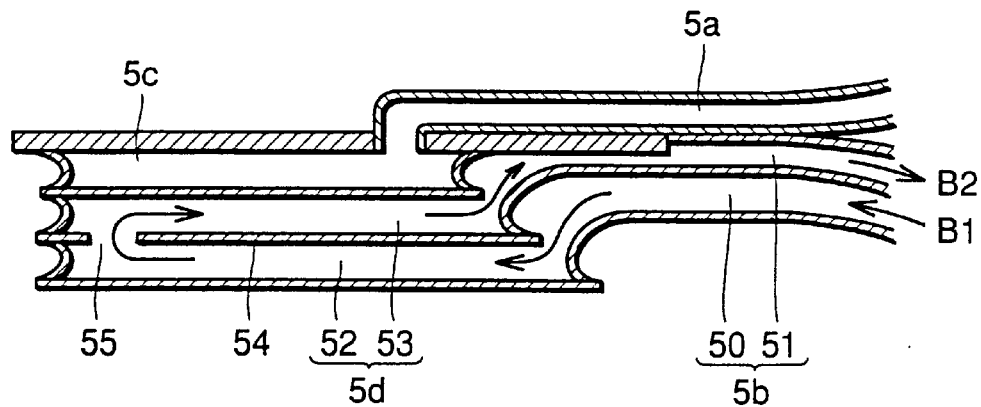
FIG. 5 is a cross sectional view taken along X—X' in FIG. 4.

Referring to FIGS. 4 and 5, second chamber 5d in probe 5B has a first auxiliary chamber 52 on the side of dura 7c, and a second auxiliary chamber 53 on the side of first chamber 5c. There is provided a partition film 54 between first and second auxiliary chambers 52 and 53. Partition film 54 has a through hole 55 at a position approximately opposite to the position to attach second tube 5b, and first and second auxiliary chambers 52 and 53 communicate with each other through through hole 55.

Second tube 5b has a first auxiliary tube 50 fixed to first auxiliary chamber 52 and a second auxiliary tube 51 fixed to second auxiliary chamber 53. Note that there is provided a gas outlet 56 to let air escape outside is provided on the side of the other end of second auxiliary tube 51 as shown in FIG. 3.

In this structure, when water is introduced as a pressure transmission medium into second chamber 5d, water may be introduced into first auxiliary chamber 52 provided on the side of dura 7c (see arrow B1 in FIG. 5) through first auxiliary tube 50, while air or the like within second chamber 5d may be discharged from the side of second auxiliary chamber 53 through second auxiliary tube 51 (see arrow B2 in FIG. 5). After the air or the like in second chamber 5d is discharged, gas outlet 56 is closed using a clip or the like (not shown).

As a result, second chamber 5d can be filled with water, as is with the probe according to the first embodiment, change in epidural pressure resulting from the pressure of first chamber 5c changed accurately according to the amount of water introduced into second chamber 5d can be measured. Accordingly, the accurate elasticity of brain parenchyma can be measured from the resultant change in epidural pressure.

Although in the second embodiment as described above, water is used as a pressure transmission medium to be introduced into second chamber 5d, the medium is not necessarily limited to water, and use of another kind of liquid such as a physiological salt solution or oil can bring about the same effects.

Figure 3:
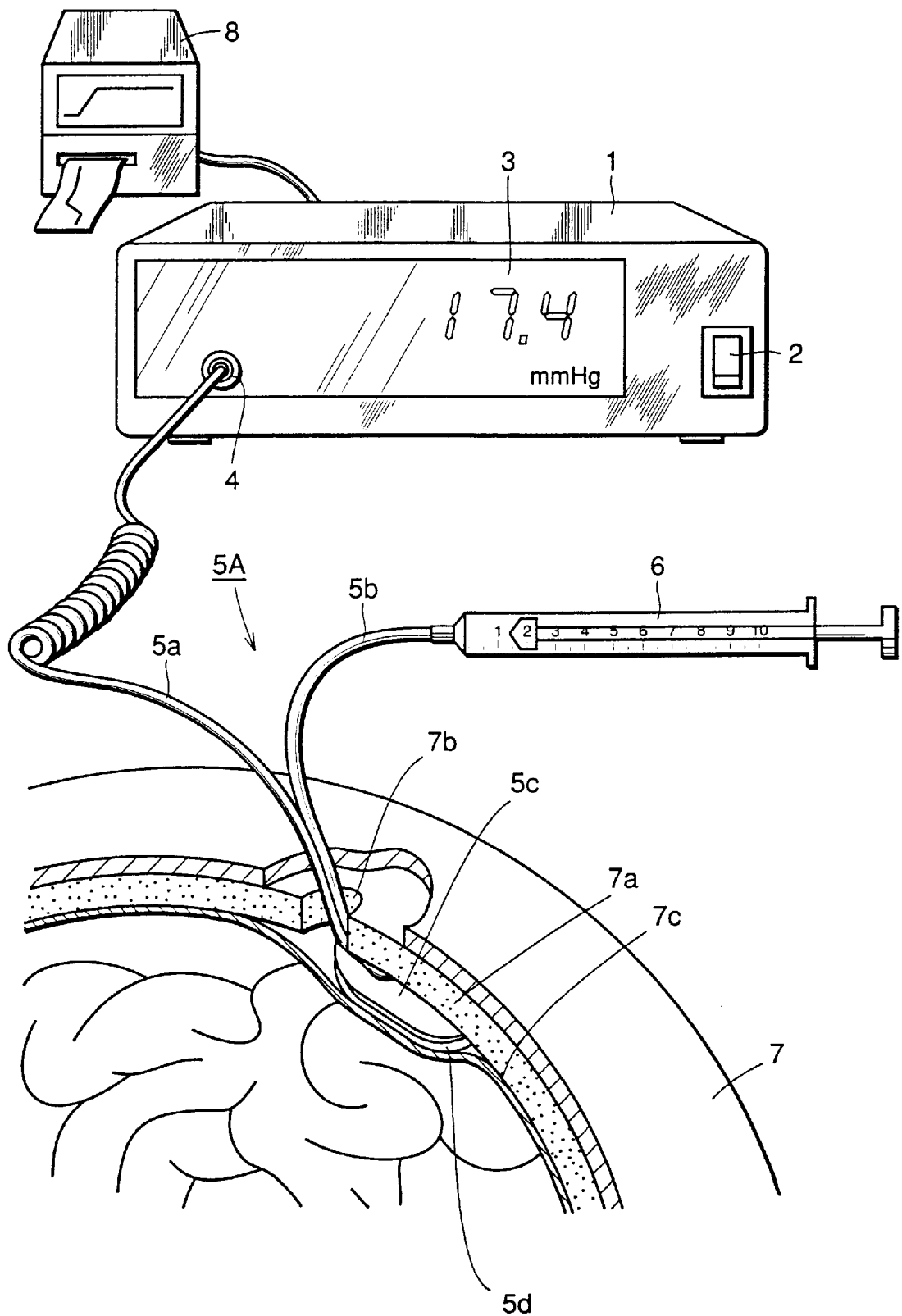
FIG. 3 is a diagram illustrating how epidural pressure and the elasticity of brain parenchyma are measured using a probe for measuring epidural pressure and the elasticity of brain parenchyma according to the present invention.

In addition, in the embodiments described above, change in epidural pressure is displayed on display 3 provided at measuring device 1, but the change may be displayed or recorded in waveform into a monitor recorder 8 connected to display 3 as shown in FIG. 3.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A probe insertable between a cranium and a dura for measuring epidural pressure and the elasticity of brain parenchyma, comprising:

a first chamber formed of a thin film with a bag-shape and adapted for placement on the side of the cranium so that said first chamber can contract/expand in response to introduction of a first pressure transmission medium;

a first tube having one end fixed to said first chamber for introducing said first pressure transmission medium into said first chamber;

a second chamber independent of said first chamber, formed of a thin film with a bag-shape and provided on the first chamber on the side of the dura so that said second chamber can contract/expand in response to introduction of a second pressure transmission medium; and a second tube having one end fixed to said second chamber for introducing said second transmission medium into said second chamber, said second tube including a first auxiliary tube fixed to said first auxiliary chamber and a second auxiliary tube fixed to said second auxiliary chamber;

said second chamber including a partition film defining a first auxiliary chamber on the side of the dura and a second auxiliary chamber on the side of said first chamber, and including a through hole at a position approximately opposite to the position for attaching said second tube, said first auxiliary chamber and said second auxiliary chamber communicating with each other through said through hole;

wherein, upon introducing and maintaining a prescribed amount of a first pressure transmission medium within said first chamber, and introducing a prescribed amount of a second pressure transmission medium into said second chamber:

epidural pressure corresponding to expansion of said first chamber is measurable at a second end of said first tube, and elasticity of brain parenchyma is measurable based on the quantity of said second pressure transmission medium introduced into said second chamber and a rate of change of epidural pressure when the prescribed quantity of said second pressure transmission medium is introduced into said second chamber.

2. The probe as recited in claim 1, wherein said first chamber, said second chamber, said first tube and said second tube are made of thermoplastic polyurethane.

3. The probe as recited in claim 1, wherein said first chamber has a substantial volume of about 0.1 ml.

4. The probe as recited in claim 1, wherein said second chamber has a variable volume in the range from 0.1 to 1.0 ml.

5. A method of measuring epidural pressure and elasticity of brain parenchyma comprising the steps:

inserting a probe, through an opening in a cranium, between a dura and the cranium;

introducing a prescribed quantity of a first pressure transmission medium into a first chamber of the probe;

measuring the epidural pressure resulting from introduction of the prescribed quantity of the first pressure transmission medium introduced into the first chamber;

introducing a second pressure transmission medium into a second chamber of the probe, while maintaining the prescribed quantity of the first pressure transmission medium within the first chamber; and measuring the elasticity of brain parenchyma based on the quantity of the second pressure transmission medium introduced in the second chamber and the rate of change of measured epidural pressure.

\* \* \* \* \*